US006289734B1

(12) United States Patent
Daugela (10) Patent No.: US 6,289,734 B1
(45) Date of Patent: Sep. 18, 2001

(54) IN-SITU NON-DESTRUCTIVE AUDIOSONIC IDENTIFICATION SYSTEM FOR VISCO-ELASTIC MATERIALS

(75) Inventor: Antanas Daugela, Minneapolis, MN (US)

(73) Assignee: Hysitron, Incorporated, Minneapolis, MN (US)

( * ) Notice: Subject to any disclaimer, the term of this patent is extended or adjusted under 35 U.S.C. 154(b) by 0 days.

(21) Appl. No.: 09/259,737

(22) Filed: Mar. 1, 1999

(51) Int. Cl.$^7$ .............................. G01N 3/48; G01M 7/00
(52) U.S. Cl. ................................ 73/573; 73/81; 73/575
(58) Field of Search .............................. 73/573, 574, 575, 73/579, 78, 81, 82, 85

(56) References Cited

U.S. PATENT DOCUMENTS

| 3,153,338 | 10/1964 | Kleesattel | 73/67.1 |
|---|---|---|---|
| 3,302,454 | 2/1967 | Kleesattel | 73/67.1 |
| 3,308,476 | 3/1967 | Kleesattel | 73/67.1 |
| 3,421,364 | 1/1969 | Moneypenny et al. | 73/82 |
| 3,472,063 | 10/1969 | Branson | 73/67.1 |
| 3,504,535 | 4/1970 | Cobb et al. | 73/86 |
| 3,836,757 | * 9/1974 | Nachtigal et al. | 73/89 |
| 4,458,694 | 7/1984 | Sollish et al. | 128/734 |
| 4,503,865 | 3/1985 | Shishido | 128/774 |
| 5,143,072 | 9/1992 | Kantorovich et al. | 128/660.02 |
| 5,298,828 | 3/1994 | Radovanovich | 310/319 |
| 5,357,786 | * 10/1994 | Lung et al. | 73/81 |
| 5,359,879 | * 11/1994 | Oliver et al. | 73/81 |
| 5,365,457 | * 11/1994 | Madigosky | 73/81 |
| 5,408,882 | 4/1995 | McKinley et al. | 73/597 |
| 5,449,370 | 9/1995 | Vaitekunas | 606/169 |
| 5,509,298 | * 4/1996 | Cheema | 73/815 |
| 5,533,339 | * 7/1996 | Gibson et al. | 73/579 |
| 5,635,664 | 6/1997 | Ishikawa et al. | 73/614 |
| 5,706,815 | 1/1998 | Sarvazyan et al. | 128/660.02 |

OTHER PUBLICATIONS

Daugela, Antanas et al., "Nondestructive Mechanical Contact Impedance and Compliance Testing Of Rubberlike Materials", *JSME International Journal*, Series A, vol. 39, No. 4., pp. 640–648 (1996).

Daugela, Antanas et al., "Measurement of the Contact Impedance of Polymers Using a Multilayered Piezo Vibroimpactor", International Symposium on Micro Machine and Human Science Proceedings., pp. 161–165 (1994).

Daugela, Antanas et al., "Contact Impedance Sensors: Applicability for the Evaluation of Flexible Structures", ASME 15$^{th}$ Bi–Annual Conference on Vibration and Noise, 8 pages (Sep. 1995).

Daugela, Antanas et al., "Modelling of Audiosonic Contact Impedance Sensor: Dynamic and Quasi–Static Treatments", *ISSN 1392–1207 Mechanika*, pp. 23–28 (1997).

* cited by examiner

Primary Examiner—Helen Kwok
(74) *Attorney, Agent, or Firm*—Dicke, Billig & Czaja, P.A.

(57) ABSTRACT

The present invention provides a portable test system for in-situ, non-destructive identification of visco-elastic material. The system includes a probe-like member coupled to a controller, wherein the controller is responsive to an output signal from the probe-like member for determining properties of the visco-elastic material. The probe-like member includes a longitudinally extending housing. A transducer mechanism is operably positioned within the housing. The transducer mechanism includes an indentation tip member, wherein the indentation tip member is extendable through the housing. A load mechanism is provided for loading the transducer mechanism with a desired constant load, causing the indentation tip member to extend through the housing to perform an indentation. A force calibration mechanism is provided for calibrating the application of a fixed force between the indentation tip member and the visco-elastic material. A mechanism is provided for applying an audiosonic signal to the visco-elastic material via the transducer mechanism, wherein response to the audiosonic signal the transducer mechanism provides an output signal representative of identification of the visco-elastic material.

16 Claims, 10 Drawing Sheets

VISCO-ELASTIC MATERIAL TABLE

| $K_1$ | $K_{21}$ | $K_{22}$ | $K_3$ | $K_4$ | Z | T | MATERIAL |
|---|---|---|---|---|---|---|---|
| A | B | C | D | E | F | G | X |
| H | I | J | K | L | M | N | $X_2$ |
| O | P | Q | R | S | T | U | $X_3$ |

222

TEST SYSTEM CONSTANTS

| $K_1$ | $K_{21}$ | $K_{22}$ | $K_3$ | $K_4$ | Z | T |
|---|---|---|---|---|---|---|
| H | I | J | K | L | M | N |

IN-SITU NON-DESTRUCTIVE AUDIOSONIC IDENTIFICATION SYSTEM FOR VISCO-ELASTIC MATERIALS

THE FIELD OF THE INVENTION

The present invention generally relates to a test system for in-situ, non-destructive identification of a visco-elastic or rubberlike material. The test system employs a unique method for identifying the visco-elastic material or identifying non-homogenous insertions or flows in the visco-elastic material.

BACKGROUND OF THE INVENTION

Visco-elastic or rubberlike materials occupy a special place in today's engineering because of the unique property of resilience. Every year scientists are reporting about new rubberlike polymers with exciting properties and potential applications for automobile, marine and aerospace industries. Despite the fact that the dynamics of rubberlike materials has been investigated intensively since early 1940s, the number of non-destructive testing methods is still limited mainly because rubberlike materials are acoustically weak, i.e., conventional ultrasonic testing is hardly applicable. Todays users are left to rely on the specification provided by a maker or manufacturer of the material.

Available non-destructive test methods are classical hardness testing and x-ray examination. Such test methods typically require large size test instruments or test instruments which are not portable and must be used in a laboratory environment. Crucial disasters due to the failure of rubberlike materials, some which have involved many casualties, illustrate a need for the highly reliable non-destructive test methods and devices. Such disasters include the explosion of the space shuttle Challenger in 1986, caused by failure of "O" rubber rings at the liquid oxygen tank and the sinking of the Estonian ferry boat in the Baltic Sea in 1995, caused by non-functioning of rubber isolation seals at the front door. It is obvious that new standards and methods for non-destructive testing of rubberlike parts in-situ should be developed in order to reliably test these materials.

SUMMARY OF THE INVENTION

The present invention provides a new test system for nondestructive identification of visco-elastic (i.e., rubberlike) materials. The system is based on simultaneous contact impedance and compliance testing, and signal processing which integrate simple rheological models into a sophisticated experimental data fitting process. Further, the test system in accordance with the present invention provides for in-situ testing, using a small, portable probe-like test member which is connectable to a portable controller or laptop computer.

The test system employs a method which may be used for both identification of visco-elastic materials and locating non-homogeneous insertions or flows in a visco-elastic material.

In one embodiment, the present invention provides a portable test system for in-situ, non-destructive identification of the visco-elastic material. The system includes a probe-like test member and a controller, wherein the controller is responsive to an output signal from the test member for determining properties of the visco-elastic material. The test member includes a longitudinally extending housing. A transducer mechanism is operably positioned within the housing. The transducer mechanism includes an indentation tip member, wherein the indentation tip member is extendable through the housing. A load mechanism is provided for loading the transducer mechanism with a desired constant load, causing the indentation tip member to extend through the housing to perform an indentation. A force calibration mechanism is provided for calibrating the application of a fixed force between the indentation tip member and the visco-elastic material. A mechanism is provided for applying an audiosonic signal to the visco-elastic material via the transducer mechanism, wherein in response to the audiosonic signal the transducer mechanism provides an output signal representative of identification properties of the visco-elastic material.

The system may further include a thermosensor which can be operably coupled to the visco-elastic material, wherein the thermosensor has an output which is representative of the temperature of the visco-elastic material at the time of the test. The force calibration mechanism may include a load pad and a spring mechanism, when the load pad is operably coupled to the probe via the spring mechanism. The load pad includes a major surface for contacting the visco-elastic material. In one aspect, the force calibration mechanism further includes a force calibration sensing mechanism. The force calibration sensing mechanism includes a proper load indicator. In another aspect, the system further includes a thermosensor, wherein the thermosensor is coupled to the load pad and is capable of measuring the temperature of the visco-elastic material at the time of the test.

In one aspect, the transducer mechanism includes a PZT actuator, a PZT sensor and a waveguide. The indentation tip member is operably coupled to a cantilever mechanism. In one preferred embodiment, the indentation tip member extends through a sidewall of the housing, and is substantially oriented perpendicular to the cantilever mechanism.

The load mechanism may include a loading plate, a mechanical linkage and a DC motor, wherein the DC motor is operably coupled to the loading plate via the mechanical linkage for controllably transferring a desired load to the loading plate. In one aspect, the mechanical linkage is a CAM system. The load mechanism may include a strain gauge, wherein the strain gauge is calibrated to the desired loading-force of the loading plate.

The controller may further include means responsive to the output signal for determining a set of material values, and a set of threshold material values corresponding to a type of visco-elastic material. In one aspect, a comparing mechanism is provided which compares the set of material values to the set of threshold material values to identify the visco-elastic material. In another aspect, a comparing mechanism is provided which compares the set of material values to the set of threshold material values to identify non-homogeneous insertions within the visco-elastic material.

In another embodiment, the present invention provides a method of identifying a visco-elastic material, including rubbers or elastomers. The method includes the step of performing an indentation on a visco-elastic material. A contact compliance test and impedance test is simultaneously performed during the indentation. A dynamic response signal is generated, wherein the dynamic response signal is representative of properties of the visco-elastic material. The dynamic response signal is filtered with a digital low-pass filter to generate an output signal waveform having a normalized amplitude. A set of test constants is determined from the output signal waveform. A table of material constants are defined for visco-elastic materials.

The test constants and the set of material constants are compared to identify the visco-elastic material.

The method may further include the step of determining the temperature of the visco-elastic material during the indentation, wherein the table of visco-elastic materials includes a temperature constant for each material.

The step of determining the set of test constants may include the step of fitting the output waveform with piece-wise polynomials. The step of fitting the output signal waveform with piece-wise polynomials may include steps of fitting a first order polynomial to a first portion of the output signal waveform to obtain a first constant, fitting a second order polynomial to a second portion of the output signal waveform to obtain a second constant and a third constant, and fitting a first order polynomial to a third portion of the output signal waveform to obtain a fourth constant.

As used herein, the term "visco-elastic" refers to rubber, rubber-like, polymers, elastomers or materials exhibiting similar characteristics.

DESCRIPTION OF THE PREFERRED EMBODIMENTS

In the following detailed description of the preferred embodiments, reference is made to the accompanying drawings which form a part hereof, and in which is shown by way of illustration specific embodiments in which the invention may be practiced. It is to be understood that other embodiments may be utilized and structural or logical changes may be made without departing from the scope of the present invention. The following detailed description, therefore, is not to be taken in a limiting sense, and the scope of the present invention is defined by the appended claims.

The present invention provides a test system for non-destructive identification of rubber-like or visco-elastic materials. The test system is based on simultaneous contact impedance and compliance testing, and signal processing which integrates simple Theological models into sophistic experimental data fitting. The present invention provides for in-situ testing, using a small, portable probe-like test member which is connectable to a portable controller or laptop computer. The test system employs a method which may be used for both identification of visco-elastic materials and locating non-homogeneous insertions or flows in a visco-elastic material.

In one embodiment, the test system is based on a simultaneous contact impedance and compliance test conducted at two different sampling frequencies which correspond to dynamic and quasi static loadings, respectively. Measurements are taken by an audiosonic, piezoactive based contact impedance tester which is a standing wave device registering the leakage of acoustic flow from the actuator via indentor into load specimens. Lames elastic constants, density and Theological parameters of the test specimen are well correlated with a change in the output signal obtained from the sensor. Experimental data are processed by means of digital filtering, auto scaling and polynomial fitting. The low-pass filter data, which corresponds to the transient of loading, are fitted with the dynamic model consisting of several Voigt's elements connected in series. Furthermore, the non-filtered data sampled at high frequency, which correspond to the quasi static loading, are compared with a data base of material properties for material identification or the identification of non-homogenous insertions or flows within the material.

Figure 1:
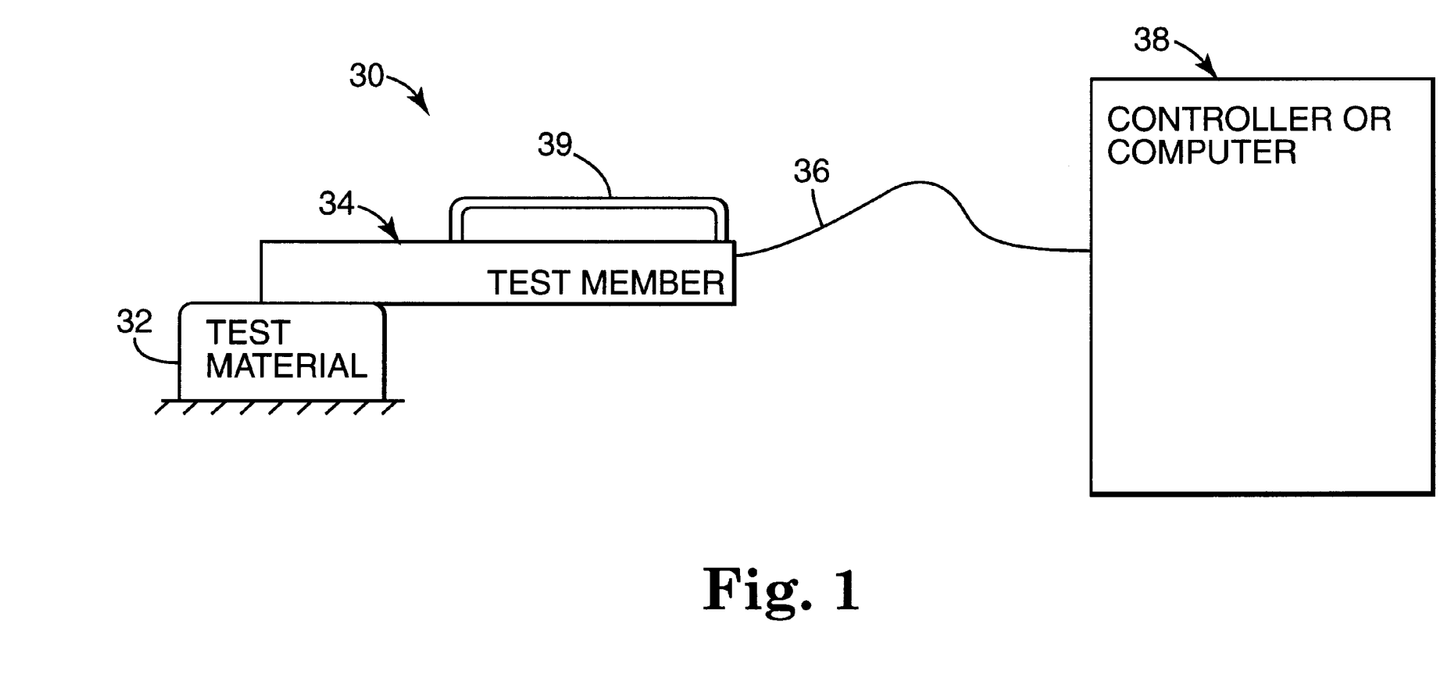
FIG. 1 is a diagram illustrating a portable test system for in-situ, non-destructive identification of visco-elastic materials, in accordance with the present invention.

In FIG. 1, one exemplary embodiment of a portable test system for in-situ, non-destructive identification of visco-elastic material (i.e., rubber-like material, elastomers or polymers) is generally shown at 30. The test system is an audiosonic, simultaneous contact impedance and compliance test system, and determines a set of test constants from the test system output which are representative of properties of the visco-elastic material. The test system monitors the material temperature at the time of the test for determination of the state of the material. Using a compare process the test constants are compared to a data base of known contstants for known materials, for identification of the material or identification of non-homogeneous insertions or flows within the material.

Test system 30 is shown operably engaged with a visco-elastic test material 32. The test system 30 generally includes a test member 34 (a probe-like or pen-like member) coupled at 36 to controller (or computer) 38. Test member 34 includes a handle 39 which aids in the handling and positioning of the test member 34. Controller 38 is responsive to an output signal or signals from test member 34 for determining properties or constants to aid in identifying the visco-elastic test material 32. Using an indentation test, test member 34 provides a simultaneous acoustic contact impedance and compliance test which is non-destructive to the test material 32. The simultaneous acoustic contact impedance and compliance test system 30 provides an output signal representative of (properties of) the test material 32. The output signal is filtered through a low-pass filter, resulting in a desired waveform. Controller 38 performs a piece-wise polynomial fitting process on the output waveform to determine a set of test constants which are representative of the test material 32. The controller 38 then compares the test constants with a table of known test constants for known materials, to identify the test material 32. Further, test system 30 includes a temperature sensor for identifying the state of test material 32.

Figure 2:
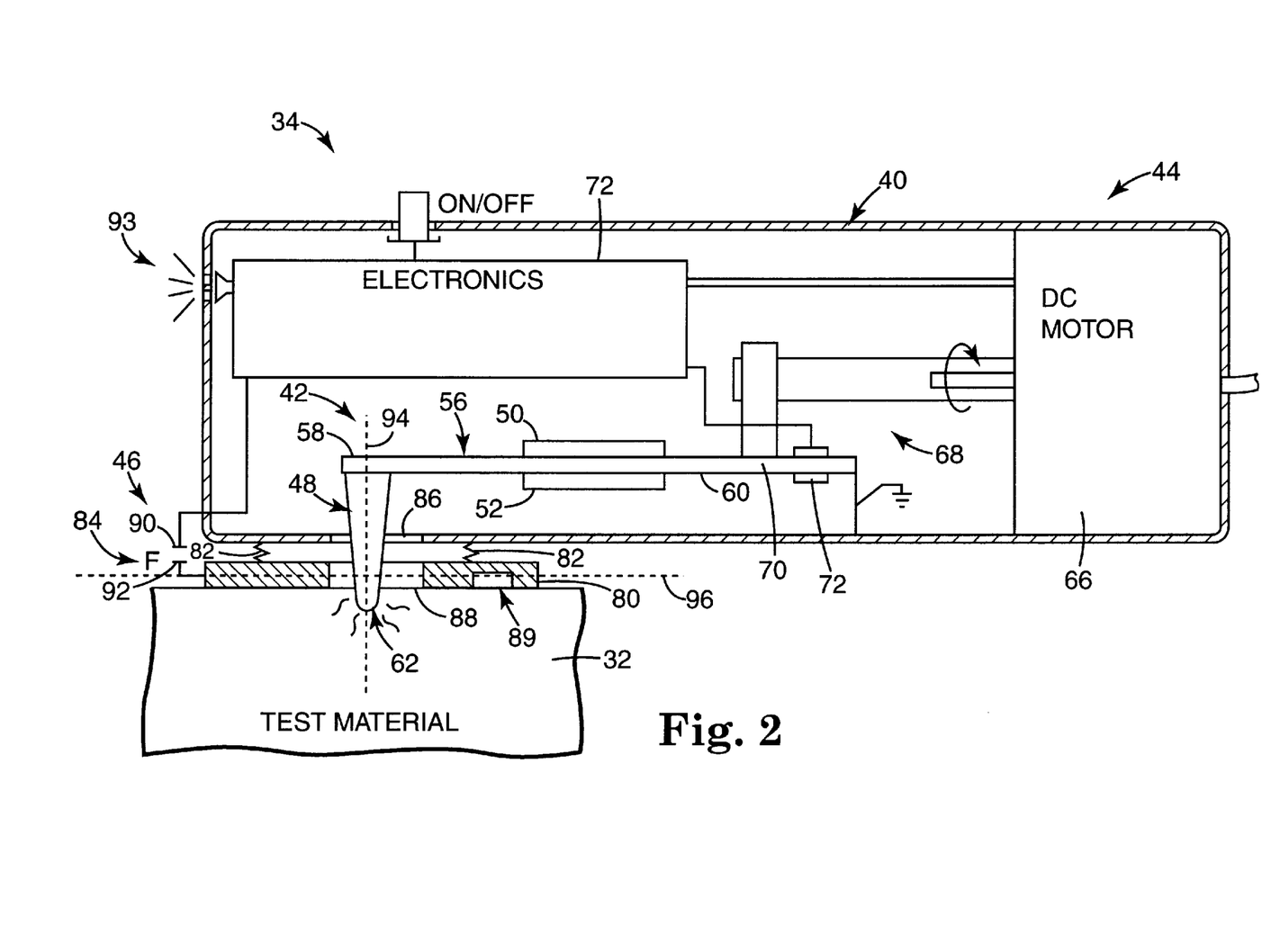
FIG. 2 is an enlarged diagram of the test member shown in FIG. 1, performing an indentation in a test material in accordance with the present invention.

FIG. 2 is a diagram illustrating one exemplary embodiment of a test member in contact with a test material 32, in accordance with the present invention. Test member 34 is a portable, small, probe-like member. In one exemplary embodiment, the test member 34 is about the size of a pen. Test member 34 includes a longitudinally extending housing, which in one exemplary embodiment is approximately the size of a pen. The housing 40 is preferably made of a rigid material, such as a metal, metal alloy, or rigid polymer or plastic.

The test member 34 further includes a transducer mechanism 42, a load mechanism 44, and a force calibration mechanism 46. The transducer mechanism 42 is operably positioned within housing 40. The transducer mechanism 42 include an indentation tip member 48, wherein the indentation tip member 48 is extendable through the housing 40 to contact the test material 32. The load mechanism 44 is utilized for loading the transducer mechanism 42 with a desired fixed load, causing the indentation tip member 48 to extend through the housing 40 to perform an indentation in test material 32. The force calibration mechanism 46 is utilized for calibrating the application of a fixed force between the indentation tip member 48 and the visco-elastic test material 32. Test member 34 including mechanisms 42, 44, 46 are described in further detail in the following paragraphs.

In one preferred embodiment, the transducer mechanism 42 includes a PZT actuator 50, a PZT sensor 52, and waveguide 54. In one aspect, waveguide 54 includes cantilever arm 56 having a first end 58 and a second end 60. Operably coupled to first end 58 is indentation tip member 48. Indentation tip member 48 is oriented substantially perpendicular to cantilever arm 56. Cantilever arm 56 is preferably made of spring steel. Indentation tip member 48 is preferably made of work hardened steel, and has a tip geometry which is, in one preferred embodiment, spherical-shaped indicated at 62. The geometry of spherical-shaped tip 62 aids in the non-destructive testing of test material 32 and provides a known localized contact area. PZT actuator 50 and PZT sensor 52 are made of piezo-ceramics. It is recognized that other tip shapes may be used.

Load mechanism 44 is utilized for loading the transducer mechanism 42. In one preferred embodiment, load mechanism 44 includes DC motor 66, mechanism linkage 68, and load plate 70. The output shaft 72 of DC motor 66 is coupled to mechanical linkage 68. In one preferred embodiment, mechanical linkage 68 comprises a cam system, and DC motor 66 is a micrometer based drive with a high gear reduction rate. Operation of DC motor 66 transfers a desired load to load plate 70 through mechanism linkage 68, which in turn causes indentation tip member 48 to perform an indentation in test material 32.

Load mechanism 44 further includes a strain gauge 72. A strain gauge 72 is operably connected to load plate 70. Strain gauge 72 is precalibrated to the desired loading force of load plate 70 to perform the indentation by indentation tip member 48. As such, once the desired load is imparted (i.e., transferred) to load plate 70, strain gauge 72 is operably coupled to test member electronics to control DC motor 66 to discontinue further loading of load plate 70.

Force calibration mechanism 46 operates to calibrate the application of a fixed force between indentation tip member 48 and the visco-elastic test material 32. In one preferred embodiment, force calibration mechanism 46 includes load pad 80, biasing or spring mechanism 82, and force indicator 84. In one preferred embodiment, load pad 80 is made of stainless steel. Load pad 80 is operably coupled to housing 40 via spring mechanism 82. Further, housing 40 include an opening 86 and load pad 80 includes an opening 88 to allow indentation tip member 48 to pass therethrough. Further, thermosensor (e.g. a thermocouple) senses the temperature of test material 32 at the time of testing, allowing the state of the material to be known. Preferably, thermosensor 89 is located on a major surface of load pad 80. Thermosensor 89 provides an output signal to controller 38 representative of the temperature or state of test material 32. For field testing environments, it is imperative that the temperature of test material 32 is known at the time of the test.

During testing of test material 32, it is desired to impart a fixed or known force to the test material 32. As such, when test member 34 is positioned against test material 32 at load pad 80, load force indicator 84 provides indication of when the proper force is applied. In one exemplary embodiment, when contacts 90, 92 meet, an electrical circuit is completed to indicate the proper force is applied. Indication of proper preloading applied force may be provided through a "beep" or a light indicator indicated at 93. During testing of test material 32, preferably indentation tip member 48 is perpendicular to the test material 32 and/or load pad 80, as indicated by perpendicular lines 94, 96.

Figure 3:
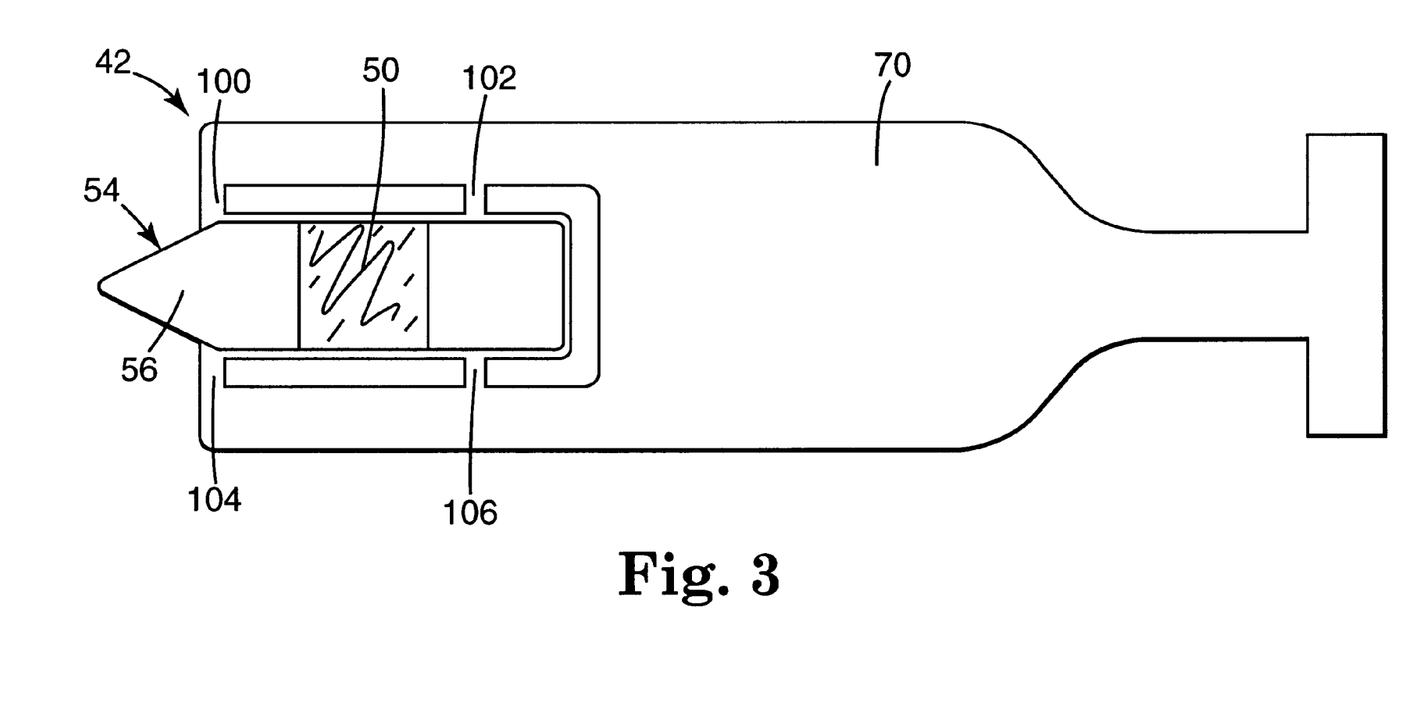
FIG. 3 is a top view illustrating a portion of the transducer shown in FIG. 2.

In FIG. 3, one exemplary embodiment is shown illustrating a top view of transducer mechanism 42. The nodes of flexural vibration are indicated at 100, 102, 104 and 106. The flexural nodes of vibration are small, mechanical connections to transducer mechanism 42.

Figure 4:
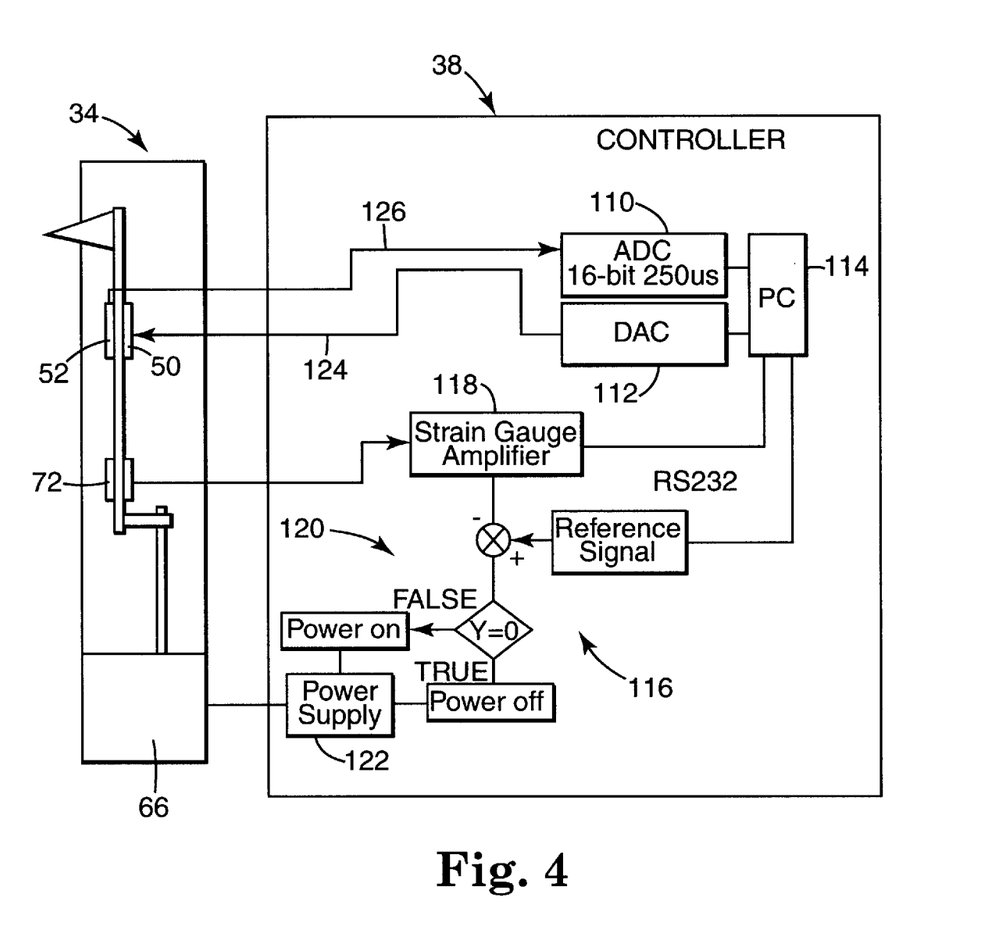
FIG. 4 is a block diagram illustrating one exemplary embodiment of the test system in accordance with the present invention.

In FIG. 4, one exemplary embodiment of a block diagram illustrating test member 34 (shown partially for clarification) coupled to controller 38 as shown. Controller 38 includes analog-to-digital converter 110 (ADC), digital-to-analog converter 112 (DAC), computer 114 (PC), and load control system 116. Load control system 116 further includes strain gauge amplifier 118, logic devices 120, and power supply 122 for controlling the load imparted to cantilever arm 56 via DC motor 66. In operation, an alternating voltage is generated by PC 114 to PZT transducer 50 through digital-to-analog converter 112. The alternating voltage excites an electrode of PZT transducer 50 at a resonance frequency, indicated at 124. An output signal 126 is provided from PZT sensor 52 which is proportional to the contact impedance and compliance obtained from the test member 34, and is input to PC 114 via the analog-to-digital converter 110.

A contact load is controlled using DC motor 66 and measured precisely using calibrated strain gauges 72 placed on the spring load plate 70. The strain gauge amplifier 118 and power source 122 are connected to the PC 114 via an RS 232 port. A contact compliance and impedance test is carried out by gradual loading of the PZT sensor 52 with a contact force.

Figure 5:
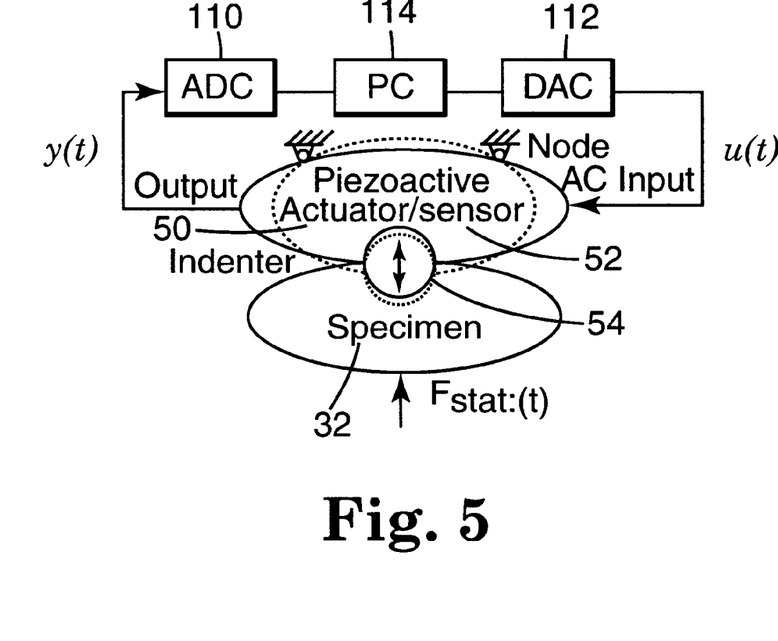
FIG. 5 is a diagram illustrating one exemplary embodiment of a partial schematic for the test system in accordance with the present invention.

The generalized schematic of the acoustic contact impedance tester 34 used for the simultaneous contact impedance and compliance measurements is shown in FIG. 5. It consists of a piezoactive (PZT) actuator 50/sensor 52 with an attached indenter which operates as wavequide 54.

The tester is operated in the resonance by the AC input u(t) applied to the PZT actuator 50. A dynamic response y(t) from the PZT sensor 52 is obtained by interaction of the direct and inverse piezo effects. Simultaneous contact impedance and compliance test is provided by slowly loading specimen test material 32 with a small contact force $F_{stat}(t)$ applied starting from zero until the constant value. AC input u(t) and control of resonance vibrations with output signal y(t) processing are performed numerically via the PC 114-DAC 112-ADC 110 circuit (See also FIG. 4).

The physical essence of ACIM measurement is to compare an acoustic contact impedance $Z_{cont}$ with the mechanical impedance of piezoactive tester $Z_{sens}$ at the driving point when the mechanical impedance of the whole specimen $Z_{spec}$ is considered to be infinitely large. When a steady state quasistatic loading is considered for evaluation ($F_{cont}$= const), impedance approach can be utilized for derivation of Acoustic Contact Impedance Evaluation (ACIE) tester analytical model. In general, impedance of the mechanical system $Z_{eqv}$ can be interpreted as a transfer function between applied force F and response velocity v obtained at the driving point:

$$F = Z_{eqv}^{-1} v \quad (1)$$

Figure 6:
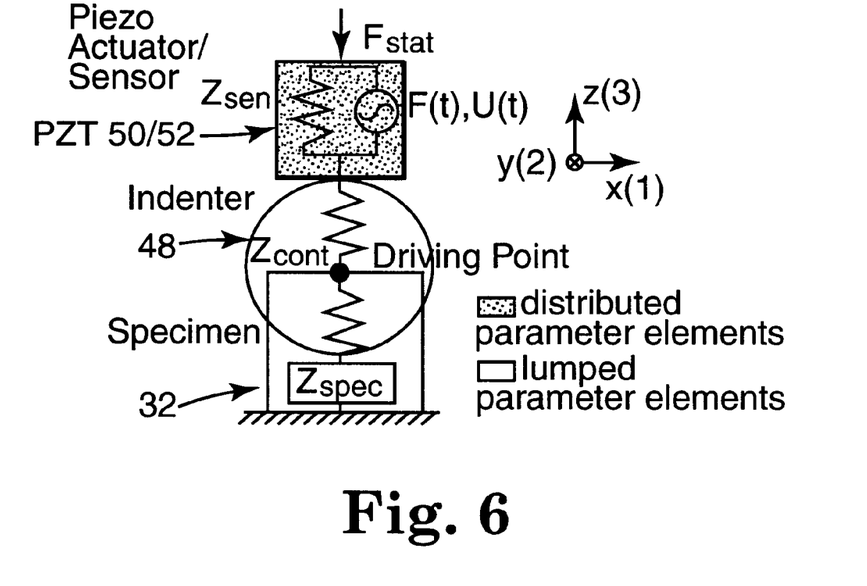
FIG. 6 is one exemplary embodiment of an impedance model of one exemplary embodiment of a test system in accordance with the present invention.

Applying Thèvenin's theorem for a one degree of freedom driving point analytical model of the piezoactive ACIE tester shown in FIG. 6, $Z_{eqv}$ can be expressed as:

$$Z_{eqv} = \sum_{i=1}^{n} Z_{sens(i)}^{-1} + Z_{cont}. \quad (2)$$

Here $Z_{sens(i)}$ is impedance of elements representing piezo tester, i.e., piezoactive component, housing frame and indenter where n is a number of elements.

A driving point impedance of the sensor can be derived from the characteristic equation of Euler-Bernoulli beam theory by taking into account corresponding boundary conditions in such a way:

$$Z_{PZT} = \frac{j2Z_{char}\cosh(h)\cos(h)}{\sinh(h)\cos(h) - \cosh(h)\sin(h)}, \quad (3)$$

where $Z_{char}$ is called the characteristic impedance and is expressed:

$$Z_{charPZT} = \rho_{PZT} A_{PZT} \sqrt[4]{\frac{I_{23PZT}\omega^2}{s_{11}^4 \rho_{PZT} A_{PZT}}}, \quad (4)$$

here, $\rho_{PZT}$—density, $A_{PZT}$—cross section area; . Parameter h is a wave number multiplied by the length of vibrating element. Impedance of the specimen can be expressed in a complex form:

$$Z_{cont} = r_{cont} + jm_{cont} - j\frac{1}{\omega q_{cont}}, \quad (5)$$

where $r_{cont}$, $m_{cont}$ and $q_{cont}$ are dissipation, inertia and contact compliance terms.

For ACIE of visco-elastic or rubberlike materials excited at audiosonic frequency $r_{cont}$ and $m_{cont}$ are negligibly small compared to the compliance term $1/\omega q_{cont}$. Then boundaries for the ACIE of elastic polymers can be formulated shortly:

$$\begin{cases} Z_{cont} \gg r_{cont}, \\ Z_{cont} \gg m_{cont}, \\ Z_{spec} \to \infty \gg Z_{cont}, \\ d_{cont} \sim 0.01\lambda. \end{cases} \quad (6)$$

Here, $d_{cont}$—diameter of elastic contact between a rigid indenter and specimen; λ—length of elastic wave propagating into the specimen.

For the normal excitation over the circular frictionless contact 62 of tip member 48, the contact compliance can be derived as follows:

$$q_{cont} = (kR_I^{0.65} x^{0.35} E_{spec})^{-1}. \quad (7)$$

A contact impedance, then:

$$Z_{cont} = -j\left(\frac{1}{\omega} kR_I^{0.65} x^{0.35} E_{spec}\right). \quad (8)$$

For the piezoactive ACIE tester, the impedance is derived from the equations of the piezo effect. The constitutive equations of the piezo effect are expressed by means of electromechanical interaction between stress T, strain S, electric field E and flux density D.

$$S_1 = s_{11}^E T_1 - d_{31} E_3, \quad (9)$$

$$D_3 = d_{31} T_1 + \epsilon_{33}^T (1 - j\delta) E_3. \quad (10)$$

here, $d_{31}$—piezoelectric constant; $s^E_{11}$—elastic constant at constant electrical field, $\epsilon^T_{33}$ dielectric permitivity at constant stress; δ—tangent of electromechanical losses. Clamping force at the driving point located between a PZT actuator and a host structure can be obtained from the equation of inverse piezo effect Eq. 9, when it is assumed that $S_1 = 0$:

$$F_{clamp} = d_{31} V_3 I_{23PZT}^{-3} (s_{11}^E)^{-1}, \quad (11)$$

here $I_{23PZT}$, $L_{PZT}$, $V_3$—inertial moment, length and voltage, respectively.

The electrical current $I_3$ on the executing electrodes can be found by integrating the flux density over the area of the electrodes:

$$I_3 = j\omega \iint_\sigma D_3 dx dy. \quad (12)$$

Substituting Eq. 8 and Eqs. 9, 10, 11 into Eq. 12 yields:

$$I_3 = j\omega b_{PZT}\left(\epsilon_{33}^T(1 - j\delta) + \frac{Z_{cont} d_{31}^2 (s_{11}^E)^{-1}}{Z_{sens} + Z_{cont}}\right) V_3, \quad (13)$$

here, $b_{PZT}$ is the width of the PZT plate.

The unknown contact mechanical impedance $Z_{cont}$ can be derived from Eq. 13 as follows:

$$Z_{cont} = Z_{sens}\left(\frac{\epsilon_{33}^T(1 - j\eta) + \frac{Y_{PZT}}{j\omega b_{PZT}}}{d_{31}^2(s_{11}^E)^{-1}} - 1\right). \quad (14)$$

Here, $Y_{PZT}$—electrical conductivity.

Equation 14 consists of capacitance admittance and the result of electromechanical interaction of the transducer 52 with the structure to be tested. In fact, Eq. 14 claims that a pure mechanical parameter of a structure can be determined from the electrical admittance of the sensor. The Vice versa statement is also right, i.e., piezoelectrical properties of the ACIE tester can be estimated when the ratio of matching impedances is known.

Figure 7:
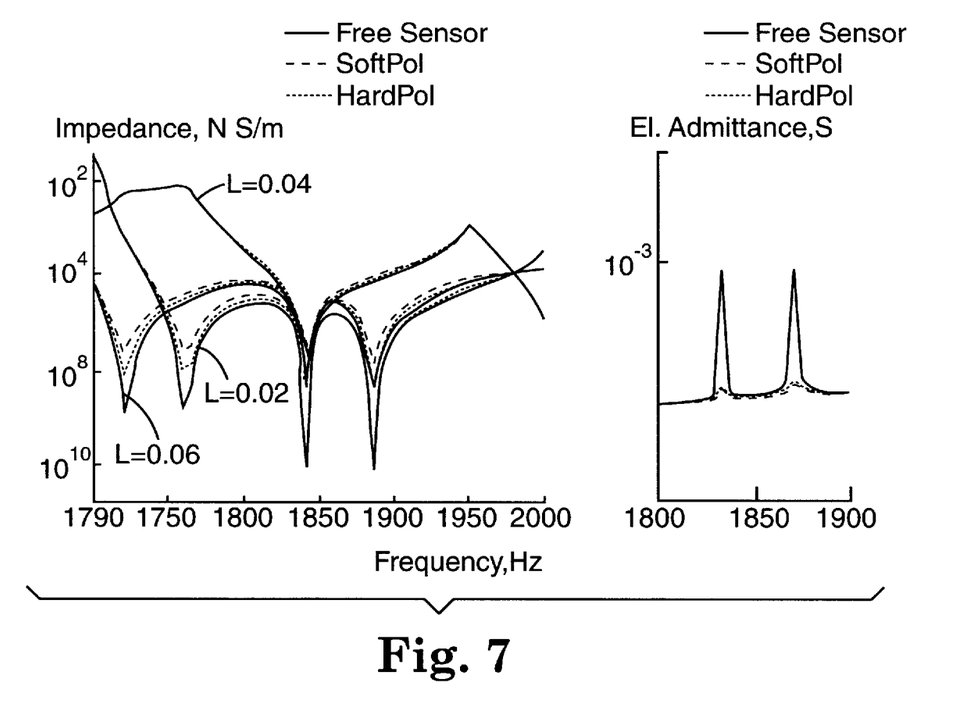
FIG. 7 includes graphs illustrating impedance and admittance, output from the test system in accordance with the present invention.

In FIG. 7, mechanical impedances and corresponding electrical admittances of loaded and unloaded analytical models are plotted versus frequency. The same resonance peak which corresponds to the PZT plate 50 can be observed for all three different lengths of the base plate ($L_{BP}$=0.02, 0.04, 0.06 m) when $L_{PZT}$=constant. It is obvious, that for more realistic modeling of loaded and unloaded sensor boundary conditions should be changed. However, it is proposed here that simple analytical model estimates matching of mechanical impedances associated with the ACIE tester and contact impedance. That is a very important design step for the ACIE tester. Further steps should be considered only after mechanical impedance match., e.g., "sculpturing" the tester by means of electromechanical FEM analysis.

Actual parameters used in calculations are summarized in the following table.

Mechanical and physical properties used in evaluation of the ACIE tester

| | |
|---|---|
| PZT MT111H, mm | 0.018 × 0.004 × 0.0005 |
| Bounded metal plate, mm | 0.04 × 0.004 × 0.0002 |
| Applied voltage $V_3$, V | 10 |
| $\rho_{PZT}$, kg/m$^3$ | 7700 |
| $\rho_{plate}$, kg/m$^3$ | 7800 |
| $M_{ind}$, kg | 0.0005 |
| $d_{31}$; m/V | $-260 \times 10^{-12}$ |
| $\epsilon^T_{33}$, F/m | $-2 \times 10^{-8}$ |
| $\delta$ | 0.025 |

Rheological Models for the ACIE based Identification.

A transient state of loading and unloading of ACIE sensor can be associated with the rheology of the specimen to be tested. In general, behavior of rubberlike materials can not be described using either by Maxwell's or Voigt's theological models. Neo-Hookian or other models should be considered for evaluation of large deformations. However, the most sophisticated is a theory developed by Bertshtein-Kersley-Zapas (BKZ) which accurately describes stress-strain transitions based on elastic strain energy for either small or large deformations. When deformation is isothermal and the material is considered to be incompressible, relaxation stresses can be expressed as the individual functions of time and deformation. Then the BKZ can give a real stress value at the moment t in the Decartian coordinate system as follows:

$$T_{ij}(t) = -p\delta_{ij} + 2\int_{-\infty}^{0} m(t-t')[h_1 F_{ij}(t, t') - h_2 c_{ij}(t, t')]dt. \quad (15)$$

Here p—hydrostatic pressure, $\delta_{ij}$ Kroneker's Delta function; $F_{ij}$ Finger's tensor of deformation, $c_{ij}$—Koshi's tensor of deformation, m(t-t')—function of "memory". In addition, Eq. 15. can be considered a generalized Boleman's principle of superpositions for large deformations where small deformations are included through functions h$_1$ and h$_2$ which contain non-linearities.

However, there always exists a tradeoff between generalized models representing physical essence and simple analytical models valid for particular cases only. One dimensional model of the visco-elastic contact can be described by combined Maxwell's and Voigt's elements. The stress at constant strain can be expressed as the sum of a number of separately relaxing Maxwell terms, thus:

$$T_i(t) = T_{i1}\exp^{\frac{-i}{\tau_1}} + T_{i2}\exp^{\frac{-i}{\tau_2}} + \ldots = \sum_{n=1}^{k} T_{in}\exp^{\frac{-i}{\tau_i}}, \quad (16)$$

$$n = 1, 2, \ldots k.$$

Each term in Eq. 18 is characterized by a distinctive relaxation time $\tau_i$. Rubberlike materials can be described by two relaxation times, one very short, as in a liquid, and one infinitely large. The first one is associated with the phenomena of local internal-molecular cohesion depending on the elastic modulus, while the second is attributed to the entropy elasticity of the molecular network. Then, a total deformation S is considered to be divisible in two parts of which the first Part $S_{0E}$ takes place substantially instantaneously, while the second part $S_{HE}$ is governed by a retardation time t' of the type which characterizes a Voigt's solid. The total deformation may then be expressed as a function of the time:

$$S(t)=S_{0E}+S_{HE}=S_{0E}+S_{HE}\infty(1-\exp'). \quad (17)$$

When the time constant t is sufficiently long, the highly elastic deformation reaches its equilibrium value $S_{HE}\infty$, corresponding to a modulus which is about 5 orders less then mentioned above. Maxwell's elements can be replaced by the Voigt elements in series. It can be shown that these two types of representation are mathematically equivalent, provided that one is allowed to include at least one 'degenerate' element of either kind, i.e., an element with either spring or the dashpot missing. This means including an element with either zero or infinite relaxation time.

This possibility is included by formulation the problem in terms of a continuous distribution, extending from t=0 to t=∞. The necessity for the inclusion of such degenerate elements can be seen by considering, for example, a material which has the property of reaching a limiting strain after a sufficient time at constant stress—a material, that is, which shows no bulk flow. It is obvious that a material of such kind cannot be represented by system of Maxwell elements in parallel unless at least one of the dashpots has infinite viscosity, i.e. does not exist. Similarly a material showing continuous flow at all times, however great, cannot be represented in terms of a Voigt model unless at least one of the elements has zero spring constant. The possibility of such transformations emphasizes the point already reffered to, that no specific correspondence is to be expected between the mathematical terms of formal model and physical or structural elements in the material.

Summarizing the discussion above it can be observed, that for describing dynamics of real indentation, multiple elements should be used instead. It can be shown that Eqs. 15–17 do not change in general for a contact deformation induced by specified geometry of indenter. If we assume that an output signal obtained from the piezoactive ACIE test system 30 correspond to the rheology of the contact indentation a piece-wise relationship should be considered where elements are controlled with selected criteria, ie., threshold values. Furthermore, an expected ACIE test system 30 output function y(t) for x∈$t_1$, $t_2$, $t_3$ can be stated consisting of three polynomial functions of the first, second and zero order, respectively.

In particular, polynomial fitting of the dynamic response is performed by means of piecewise polynomial fitting procedure. A typical loading process of the spherical indenter indenting into a visco-elastic specimen can be approximated by three zones. A standard Legandre polynomial data fitting procedure for each of the segments individually is applied here. First and second order Lagandere polynomial has been used. In general, Legandre polynomial fitting procedure is explained in most of book on numerical signal processing or data fitting.

Separation into the segments is performed by using threshold value approach. Threshold value is a tolerance for the data scattering at the corresponding region (zone). Tolerance value is obtained from experiments and it is assumed to be at a margin of 0.015y. However, Tolerance also depends on resolution and noise floor of the data acquisition system.

$$\alpha, \beta, \gamma = 1 \pm \text{Tolerance}$$

An experimental data record of it starts when a corresponding signal is received informing that a pre-loading force on the load pad is obtained. First point for polynomial fitting treatment is obtained when indenter touches the surface.

$$y(t) = \begin{cases} -\alpha K_1 x, & x \in t_1 \\ -K_{21} \exp^{-\beta K_{22} x}, & x \in t_2 \\ -\gamma K_3, & x \in t_3 \end{cases} \quad (18)$$

$K_3 = y(t) = $ constant. This is a stabilized state of the indent, when a loading force is constant and deformed material Theological behavior at the local contact is stabilized.

Information for the unloading process can be processed in the same way.

Here, $\alpha, \beta, \gamma$ are threshold values controlling the influence of each element; $K_{1-3}$—coefficients returned by a fitting procedure performed by controller 38. Constants (i.e., coefficients) $K_1$, $K_{21}$, $K_{22}$, $K_3$ can be used to identify test material 32.

The following paragraphs illustrate an example of how a material can be identified using the test system of FIGS. 1–7.

In specific reference to FIGS. 1–4, testament material 32 is operably engaged by test number 34. An alternating input voltage of 10 volts is generated by controller 38 via PC 114 and digital-to-analog converter 112, indicated at 124. This input signaling excites an electrode of the PZT transducer 50 at a resonance frequency of 1.801 kilohertz. An output signal which is proportional to the contact impedance in compliance is obtained by controller 38 from the PZT sensor 52 via the analog-to-digital converter 110 to PC 114. In the exemplary embodiment, the output signal was taken with a 250 microsecond sampling time.

The contact load was controlled using a micrometer-based drive DC motor 66 and measured using precisely calibrated strain gauge 72 placed on the spring load plate 70. The strain gauge amplifier 118 and power supply 122 are connected to PC 114 via an RS 232 port. The contact compliance and impedance test is carried out by gradually loading of the transducer 42 with a contact force from 0 to 0.05 neutons (N). Measurements are performed at a loading speed of 0.26 mm/sec.

Figure 8:
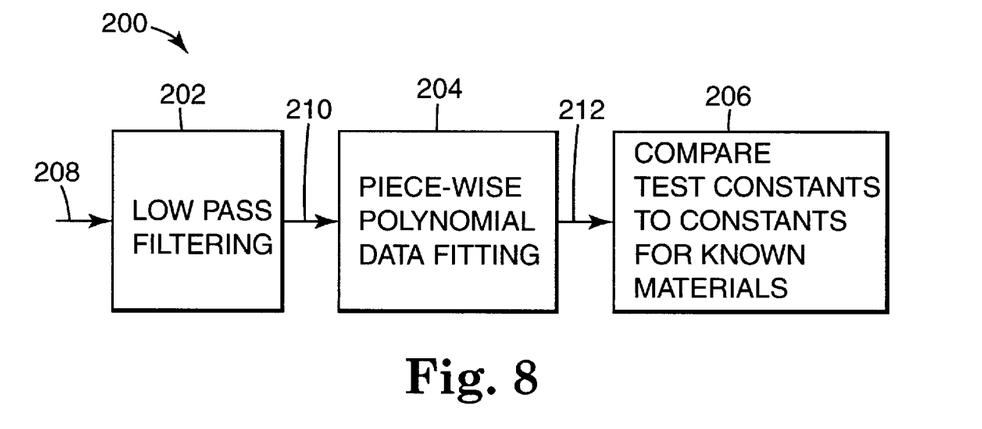
FIG. 8 is a block diagram illustrating one exemplary embodiment of signal processing in accordance with the present invention.
Figure 9:
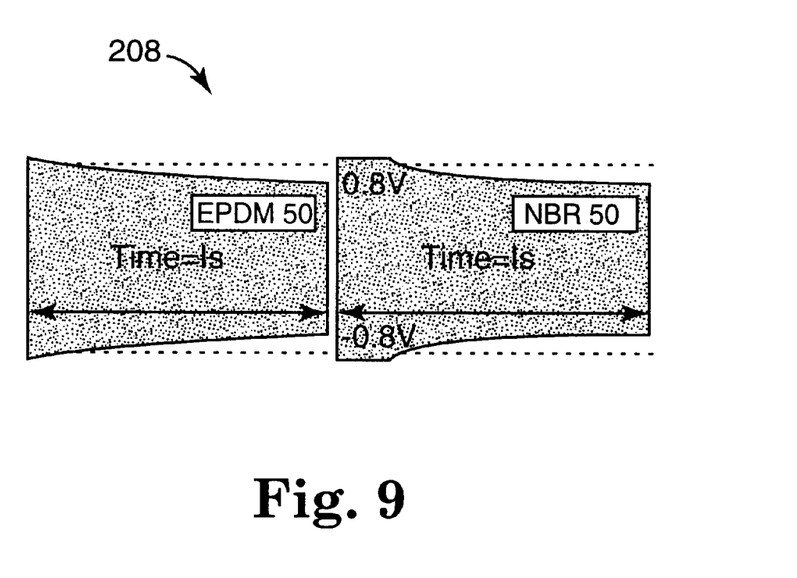
FIG. 9 is a graph illustrating one exemplary embodiment of a dynamic response obtained from the test system in accordance with the present invention of two different test materials made of EPDM 50 and NBR 50 having the same hardness.

PC 114 performs the signal processing of output signal 126 via analog-to-digital converter 110. The signal processing performed by controller 38 is illustrated in FIG. 8 at 200. The signal processing procedure includes low pass filtering 202, piece wise polynomial date fitting 204, and compare test constants to constants for known materials 206. A typical dynamic response output signal obtained from the test member 34 via analog-to-digital converter 110 (from PTZ sensor 52) during simultaneous contact compliance and impedance testing is indicated at 208, and shown in FIG. 9. A sharp change in mechanical impedance is observed caused by a leakage in acoustic flow during indentation. The two different specimens illustrated made of NBR and EPDM have the same hardness, but act differently and have difference in amplitude in the range of 30 mV. This indicates that only the mechanical impedance component Z is not enough for identification of different visco-elastic materials. However, the correlation between actual mechanical and physical properties is found to be in the range of 0.99.

Among the practically measured mechanical parameters the Young's modulus, Hardness and coefficient of viscosity are the most important. The damping of the amplitude during ACIE of specimens made of NBR having 20 and 90 IRHD was 2.5 dB. This gives enough resolution for the entire measuring range.

Figure 10:
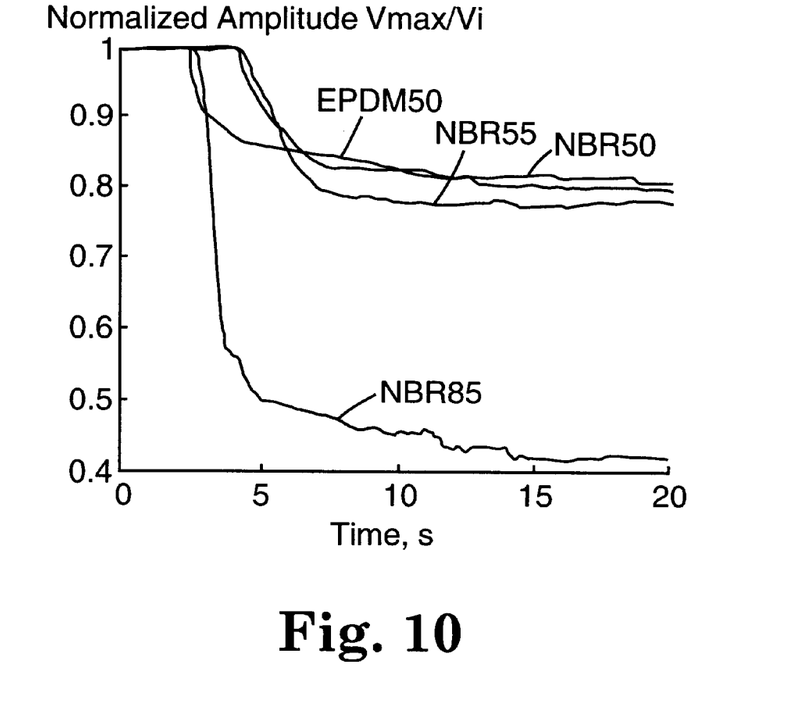
FIG. 10 is a graph illustrating output signals obtained from the identification test system in accordance with the present invention plotted versus time after low-pass filtering for different visco-elastic materials.
Figure 11:
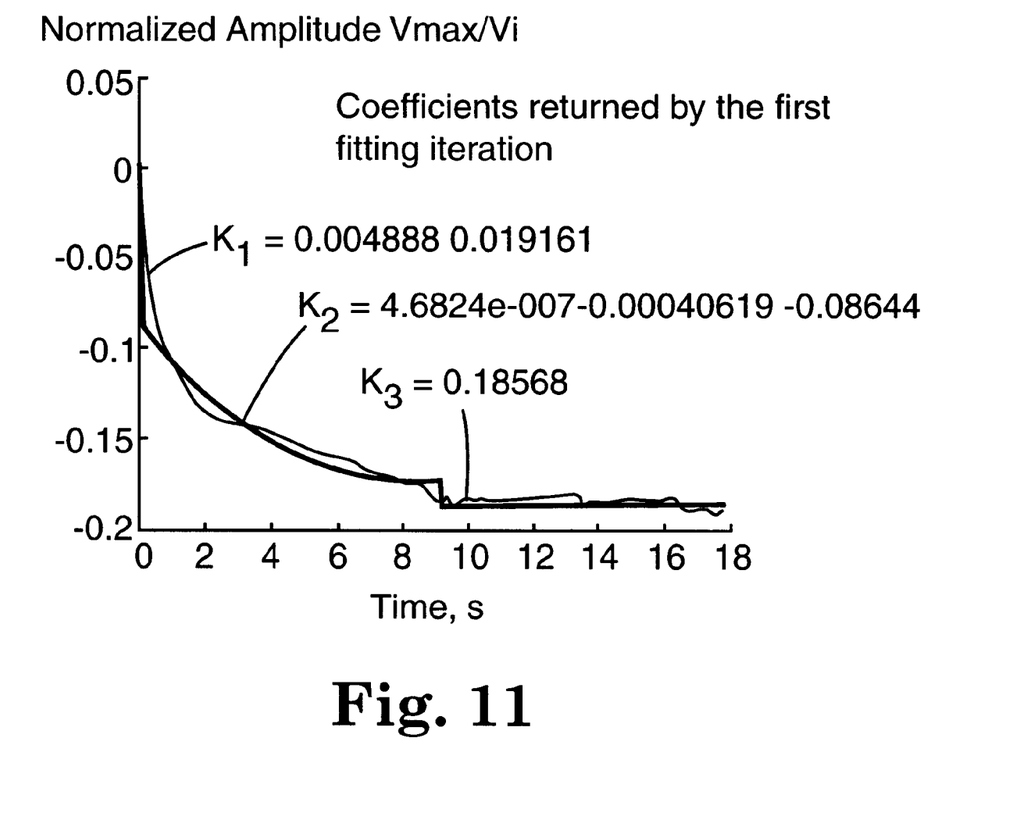
FIG. 11 is a graph illustrating the obtaining of co-efficients by fitting the output signal data with piece-wise polynomials, in accordance with the present invention.

Output signal 210 as a result of LP filtering 202 is shown in FIG. 10. The LP filtering 202 separates what we can call the "DC component" and corresponds to the contact compliance taken during the process of loading. (shown for materials EPDM 50, NBR 55, NBR 50 and NBR 85) FIG. 11 illustrates a first iteration for piece-wise polynomial fitting performed on the filtered signal, indicated by output 212. The iterative fitting process returns polynomial coefficients that are used in material characterization. Threshold values $\alpha$, $\beta, \gamma$ are controlled by software and chosen during calibration of the system. A zero order polynomial (Eq. 18) returns value $K_4$ which is proportional to the static contact compliance. $K_3$ for EPDM and NBR materials are about the same because of digitization, LP filtering and threshold tolerances, i.e., they give the same value of hardness as a conventional micro hardness test.

Thus, each material can be characterized by the set of coefficients Index or contrast describing dynamics of the ultrasonic indentation:

$$\text{Index} = [K_{11}, K_{12}, K_{21}, K_3, K_4, Z, T]. \quad (19)$$

As previously described herein constants $K_1$, $K_{21}$, $K_{22}$ and $K_3$ are derived from the process of piecewise polynomial fitting. Constant $K_4$ is obtained by the zero order polynomial (equation 18) which is proportional to the static contact compliance. Z is the audiosonic contact impedance and T is the temperature of the test material 32 at the time of testing obtained by thermal sensor 98. The temperature constant of test material 32 is extremely important for in-situ testing. In a conventional laboratory environment, the ombiant temperature within the lab is controlled. In contrast, it is important to know the temperature when utilizing test system 30 as a portable unit under field test conditions. This is extremely important since the properties of visco-elastic materials change with temperature.

Figure 12:
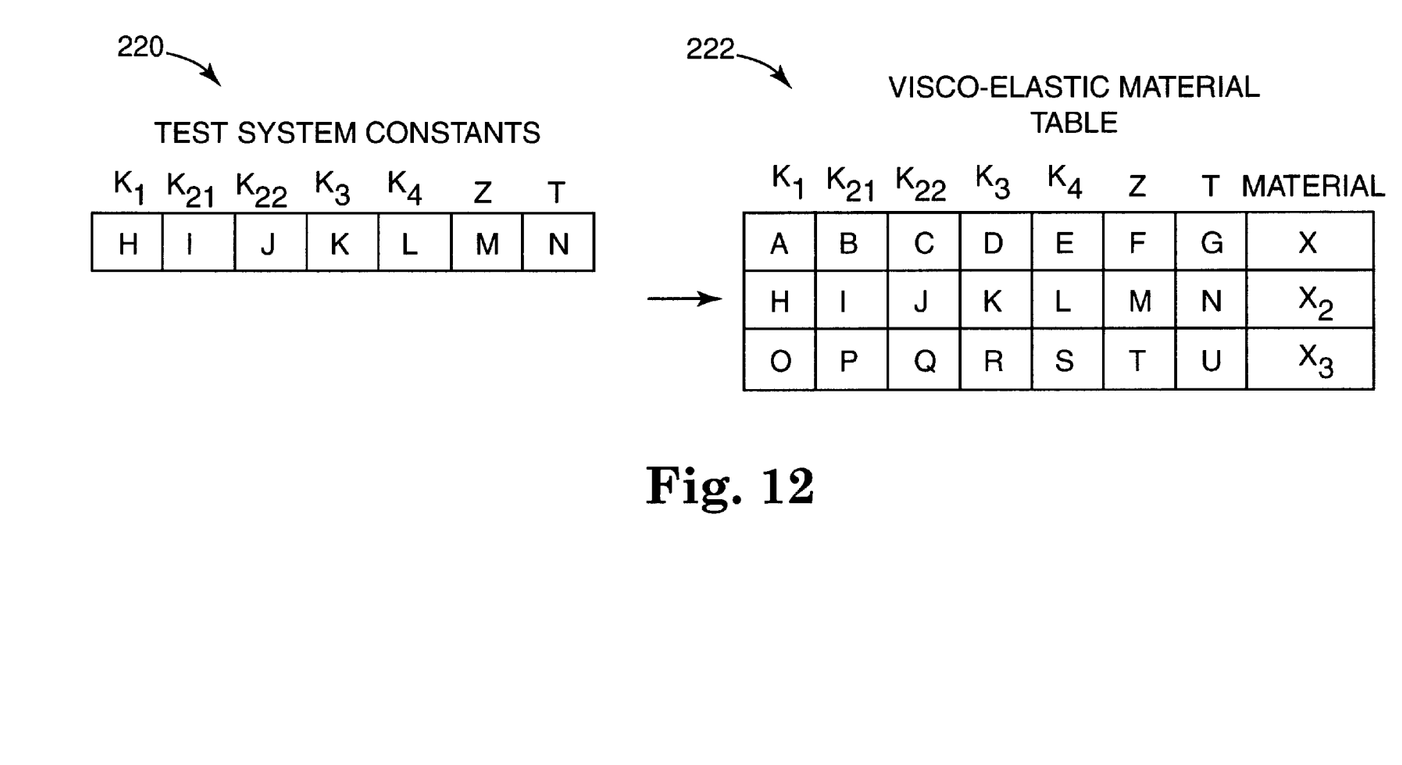
FIG. 12 is a diagram illustrating one exemplary embodiment of a compare process using test constants to identify a material, in accordance with the present invention.

The process of nondestructive identification relies on statistical comparison of Index (i.e., the index constants or test constants) between a database and the specimen to be characterized. The process 206 of comparing test constants to constants for known materials is illustrated in FIG. 12. The test system constants obtained from the testing of test material 32 by test member 34 are indicated at 220. Table 222 comprises a database of known constants for visco-elastic materials. The table is contained in memory in PC 114. The test system constants are compared to the constants contained within the visco-elastic material table 222, for identification of the test material 32 or associating properties of the test material with a known material. In the exemplary embodiment shown, the test material 32 is identified as having properties associated with material X2. Alternatively, the present invention can be used for identifying non-homogenous insertions or flows within a known material. In this embodiment, if the test system constants 220 fall outside of a range of values for the test constants for the known material, a non-homogenous insertion or flow is identified.

Figure 13:
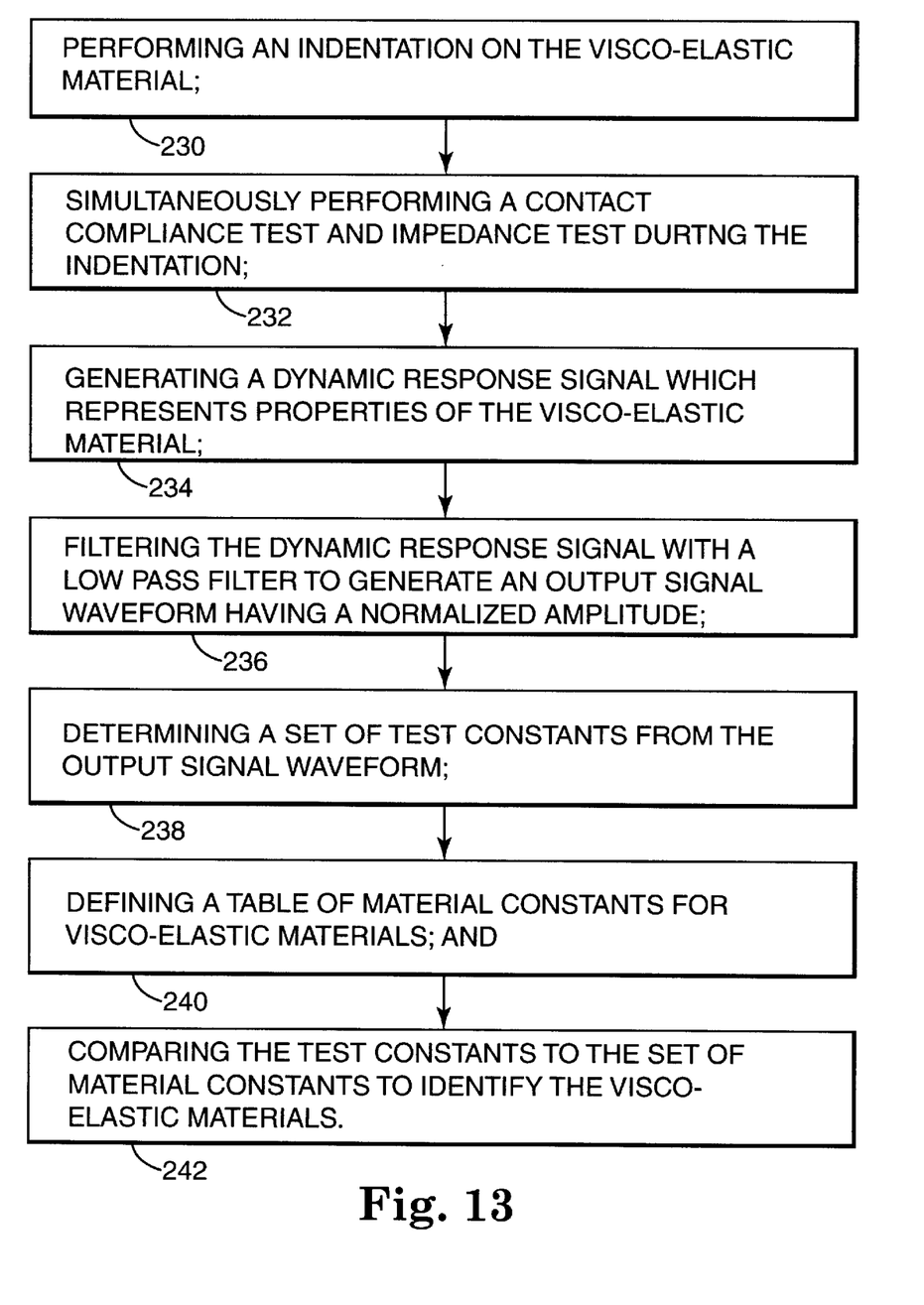
FIG. 13 is a block diagram illustrating one exemplary embodiment of a method for identifying a visco-elastic material in accordance with the present invention.

FIG. 13 is a block diagram illustrating one exemplary embodiment of a method of identifying a visco-elastic material including rubbers or elastomers, employed by the portable test system for in-situ nondestructive identification of a visco-elastic material in accordance with the present invention. In step 230, an indentation is performed on the visco-elastic material. In step 232, a contact compliance test and impedance test are simultaneously performed during the indentation.

In particular, the PZT actuator 50 is calibrated by applying a resonance frequency to the PZT actuator 50. At the same time, the output signal from PZT sensor 52 is monitored to evaluate the resonance state. The frequency is tuned by finding the highest amplitude output in the time domain to determine the natural resonance state of the transducer 50.

For visco-elastic materials, the resonance of frequency is in the audiosonic range. Since the material structure is rather flexible, the frequency drops within the audiosonic range of approximately 2 kilohertz, wherein the audiosonic range is between 1 hertz to 22 kilohertz. Once calibrated, the resonance frequency is fixed (while the tip is not touching anything).

The test member 34 is positioned on the surface of test material 32. The proper preload is applied when indicated by the preload proper load indicator 46 (e.g., via a "beep").

Once the proper preload force is obtained, the load mechanism 44 is activated to transfer a load to test material 32 via loading plate 70 and tip 48. During this time, the calibrated resonance frequency signal continues to be applied. The load is applied with a constant velocity via the PC 114 and DAC 112 to send a well-defined DC voltage to motor 66.

When the tip 48 touches the test material 32, the sensor vibrates in standing wave mode. The nodes of vibration, amplitude of vibration is zero. Loading usually takes approximately 5 seconds. As the transducer is approaching the surface and the tip member 48 touches the test material 32, stiffness is added to the sensor mechanism and the standing wave mode vanishes. In particular, the excitation frequency of the PCT actuator is still fixed at the previously calibrated natural resonance frequency, but the natural frequency of the oscillating system switches because of the added stiffness due to the test material 32. As the tip 48 performs the indentation in test material 32, acoustic flow generated at the transducer leaks through the local contact area of the indentor 48 (at tip 62) and test material 32. As the sensor 52 changes from the resonance state, material identification information is obtained (as shown in FIGS. 7–11). The loading and resulting indentation is performed until strain gauge 72 indicates that the desired loading force has been obtained.

Similar to the loading process of the test material, it is also recognized that test constants can be obtained from a dynamic response signal taken during unloading of the test material. The additional coefficients derived from the unloading curves may be further helpful to identify or categorize the test material. Although it may be beneficial to extend the test system to include a dynamic response signal generated during unloading of the test material 32, it may be impractical due to the additional time added to the test procedure. For example, an additional unloading process may extend the time of the test procedure from 5 seconds to 10 seconds.

In step 234, a dynamic response signal representative of properties of the visco-elastic material is generated, being formed from PZT sensor 52. In step 236, the dynamic response signal is filtered with a low-pass filter (e.g., a digital low-pass filter) to generate an output signal waveform having a normalized amplitude. In step 238, a set of test constants (i.e., Index) are determined from the output signal waveform. In step 240, a table of material constants is defined for known visco-elastic materials. In step 242, the test constants are compared to the set of material constants to identify or categorize the visco-elastic material.

In one embodiment, the method includes the step of determining the temperature of the visco-elastic material during the indentation, wherein the table of visco-elastic materials includes a temperature constant for each material. The step of determining the set of test constants includes the step of fitting the output signal waveform with piecewise polynomials. The step of fitting the output waveform with piecewise polynomials includes the steps of fitting a first order polynomial to a first order polynomial to a first portion of the output signal waveform to determine a first material constant, fitting a second order polynomial to a second portion of the output signal waveform to determine a second material constant and a third material constant, and fitting a first order polynomial to a third portion of the output signal waveform to determine a fourth material constant.

In summary, a new nondestructive identification system is developed for evaluation of mechanical characteristics of rubberlike materials. The identification system rely on the simultaneous mechanical contact impedance and compliance evaluation which can be considered as a successful combination of the existing classical micro hardness testing methods and ultrasonic indentation techniques.

An impedance test should be performed at the high sampling frequency (100 kHz) in order to obtain reliable dynamic response caused by the vanished standing wave of free ACIE tester vibrations. Also, the impedance test should be carried out at the steady state of ultrasonic vibrations. The 2.5–4 dB output signal obtained from the sensor highly correlates with mechanical characteristics such as Young's modulus, hardness, density and damping parameters.

LP filtered experimental data are fitted with the curves associated with linear Theological models. Since behavior of rubberlike materials in general does not correspond exactly to either the Maxwell or Voigt models it is necessary to use multiple elements instead For softer specimens, Voigt's model is used and for the hard rubbers a combined Voigt-Maxwell's Theological model with neglected damping member is employed. The proposed simple polynomial fitting technique and evaluation process were found to be efficient in order to perform identification of the unknown rubberlike specimens made of NBR, EPDM polymers and natural rubber.

The mechanical impedance approach is introduced for derivation of electromechanical characteristics of the PZT ACIE tester. Therefore, the impedance model is of great importance for system and control engineers because it directly returns a transfer function. An ultrasonic indentation, particularly ACIE method, can not be treated as an ordinarily control identification problem, ie., analyzed by random or chirp inputs because of the narrow operation bandwidth.

Although specific embodiments have been illustrated and described herein for purposes of description of the preferred embodiment, it will be appreciated by those of ordinary skill in the art that a wide variety of alternate and/or equivalent implementations calculated to achieve the same purposes may be substituted for the specific embodiments shown and described without departing from the scope of the present invention. Those with skill in the chemical, mechanical, electromechanical, electrical, and computer arts will readily appreciate that the present invention may be implemented in a very wide variety of embodiments. This application is intended to cover any adaptations or variations of the preferred embodiments discussed herein. Therefore, it is manifestly intended that this invention be limited only by the claims and the equivalents thereof.

What is claimed is:

1. A portable test system for in-situ, non-destructive identification of a visco-elastic material, the system comprising:
   a probe-like test member and a controller, the probe-like test member having at least one output signal representative of the visco-elastic material, wherein the controller is responsive to the output signal for determining properties of the visco-elastic material, the test member comprising:
     a longitudinally extending housing;
     a transducer mechanism operably positioned within the housing, the transducer mechanism including an indentation tip member, wherein the indentation tip member is extendable through the housing;
     a load mechanism for loading the transducer mechanism with a desired constant load, causing the indentation tip member to extend through the housing to perform an indentation on the visco-elastic material;
     a force calibration mechanism for calibrating the application of a fixed force between the indentation tip member and the visco-elastic material; and
     the controller including a mechanism for applying an audiosonic signal to the visco-elastic material via the transducer mechanism, where in response to the audiosonic signal the transducer mechanism provides an output signal representative of identification of the visco-elastic material, the controller including means responsive to the output signal for determining a set of material values using mechanical contact impedance matching and piecewise polynomial fitting; and a set of threshold material values corresponding to a type of visco-elastic material.

2. A portable test system for in-situ, non-destructive identification of a visco-elastic material, the system comprising:
   a probe-like test member and a controller, the probe-like test member having at least one output signal representative of the visco-elastic material, wherein the controller is responsive to the output signal for determining properties of the visco-elastic material, the test member comprising:
     a longitudinally extending housing;
     a transducer mechanism operably positioned within the housing, the transducer mechanism including an indentation tip member, wherein the indentation tip member is extendable through the housing;
     a load mechanism for loading the transducer mechanism with a desired constant load, causing the indentation tip member to extend through the housing to perform an indentation on the visco-elastic material;
     a force calibration mechanism for calibrating the application of a fixed force between the indentation tip member and the visco-elastic material;
   the controller including a mechanism for applying an audiosonic signal to the visco-elastic material via the transducer mechanism, where in response to the audiosonic signal the transducer mechanism provides an output signal representative of identification of the visco-elastic material; and
     a thermosensor which can be operably coupled to the visco-elastic material.

3. The system of claim 1, wherein the force calibration mechanism includes a load pad and a spring mechanism, wherein the load pad is operably coupled to the probe-like test member via the spring mechanism, the load pad including a major surface for contacting the visco-elastic material.

4. The system of claim 3, wherein the force calibration mechanism further includes a force calibration sensing mechanism.

5. The system of claim 4, wherein the force calibration sensing mechanism includes a proper load indicator.

6. The system of claim 3, the system further comprising a thermosensor, wherein the thermosensor is coupled to the load pad and is capable of measuring the temperature of the visco-elastic material.

7. The system of claim 1, wherein the transducer mechanism includes a PZT actuator, a PZT sensor and a waveguide.

8. The system of claim 1, wherein the indentation tip member is operably coupled to a cantilever mechanism.

9. The system of claim 1, wherein the load mechanism includes a loading plate, a mechanical linkage and a DC motor, wherein the DC motor is operably coupled to the loading plate via the mechanical linkage for controllably transferring a desired load to the loading plate.

10. The system of claim 9, wherein the mechanical linkage is a cam system.

11. The system of claim 9, wherein the load mechanism includes a strain gauge, wherein the strain gauge is calibrated to the desired loading of the loading plate.

12. The system of claim 1, further comprising a comparing mechanism which compares the set of material values to the set of threshold material values to identify the visco-elastic material.

13. The system of claim 1, further comprising a comparing mechanism which compares the set of material values to the set of threshold material values to identify non-homogeneous insertions within the visco-elastic material.

14. A method of identifying a visco-elastic material, including rubbers or elastomers, the method comprising the steps of:
   performing an indentation on the visco-elastic material;
   simultaneously performing a contact compliance test and impedance test during the indentation;
   generating a dynamic response signal representative of properties of the visco-elastic material;
   filtering the dynamic response signal with a low pass filter to generate an output signal waveform having a normalized amplitude;
   determining a set of test constants from the output signal waveform, using mechanical contact impedance matching and fitting the output signal waveform with piecewise polynomials;
   defining a table of material constants for one or more visco-elastic materials; and
   comparing the set of test constants to the table of material constants to identify the visco-elastic material.

15. A portable test system for in-situ, non-destructive identification of a visco-elastic material, the system comprising:
   a probe-like test member and a controller, the probe-like test member having at least one output signal representative of the visco-elastic material, wherein the controller is responsive to the output signal for determining properties of the visco-elastic material, the test member comprising:

a longitudinally extending housing;

a transducer mechanism operably positioned within the housing, the transducer mechanism including an indentation tip member, wherein the indentation tip member is extendable through the housing;

a load mechanism for loading the transducer mechanism with a desired constant load, causing the indentation tip member to extend through the housing to perform an indentation on the visco-elastic material;

a force calibration mechanism for calibrating the application of a fixed force between the indentation tip member and the visco-elastic material;

the controller including a mechanism for applying an audiosonic signal to the visco-elastic material via the transducer mechanism, where in response to the audiosonic signal the transducer mechanism provides an output signal representative of identification of the visco-elastic material; and determining the temperature of the visco-elastic material during the indentation, wherein the table of material constants includes a temperature constant for each material.

16. The method of claim 14, wherein the step of fitting the output signal waveform with piecewise polynomials includes the steps of fitting a first order polynomial to a first portion of the output signal waveform, fitting a second order polynomial to a second portion of the output signal waveform, and fitting a third order polynomial to a third portion of the output signal waveform.

* * * * *